United States Patent [19]

Heske

[11] Patent Number: 5,535,755
[45] Date of Patent: Jul. 16, 1996

[54] TISSUE SAMPLER

[76] Inventor: Norbert Heske, Am Brand 1, D-8087 Tuerkenfeld, Germany

[21] Appl. No.: 352,098

[22] Filed: Nov. 30, 1994

Related U.S. Application Data

[63] Continuation-in-part of Ser. No. 143,389, Oct. 29, 1993, abandoned, which is a continuation of Ser. No. 995,934, Dec. 22, 1992, abandoned, which is a continuation of Ser. No. 671,908, filed as PCT/DE90/00549, Jul. 20, 1990, abandoned.

[30] Foreign Application Priority Data

Jul. 22, 1989 [DE] Germany ............. 39 24 291.9

[51] Int. Cl.⁶ ...................................... A61B 10/00
[52] U.S. Cl. ................................................ 128/754
[58] Field of Search ..................... 128/749, 751–754; 606/167, 170, 171

[56] References Cited

U.S. PATENT DOCUMENTS 4,735,215  4/1988  Goto et al. ...................... 128/754
4,881,551  11/1989  Taylor ............................. 128/754

FOREIGN PATENT DOCUMENTS 0173653  3/1986  European Pat. Off. .
0207726  1/1987  European Pat. Off. .
0238461  9/1987  European Pat. Off. .

Primary Examiner—Max Hindenburg
Attorney, Agent, or Firm—Evenson, McKeown Edwards & Lenahan

[57] ABSTRACT

A device for taking tissue samples by means of a biopsy cannula comprising a needle element with a cavity in its distal terminal zone and an exterior tube surround the needle element, which cannula is inserted into the tissue to be sampled by means of an inserting unit. The inserting unit causes the needle element and the exterior tube to move together into a position inside the tissue in which the exterior tube is pushed over the cavity, the inserting unit retracts the exterior tube behind the cavity in the needle element after termination of the inserting operation, and subsequently pushes the exterior tube again over the needle element so as to cover the cavity.

15 Claims, 4 Drawing Sheets

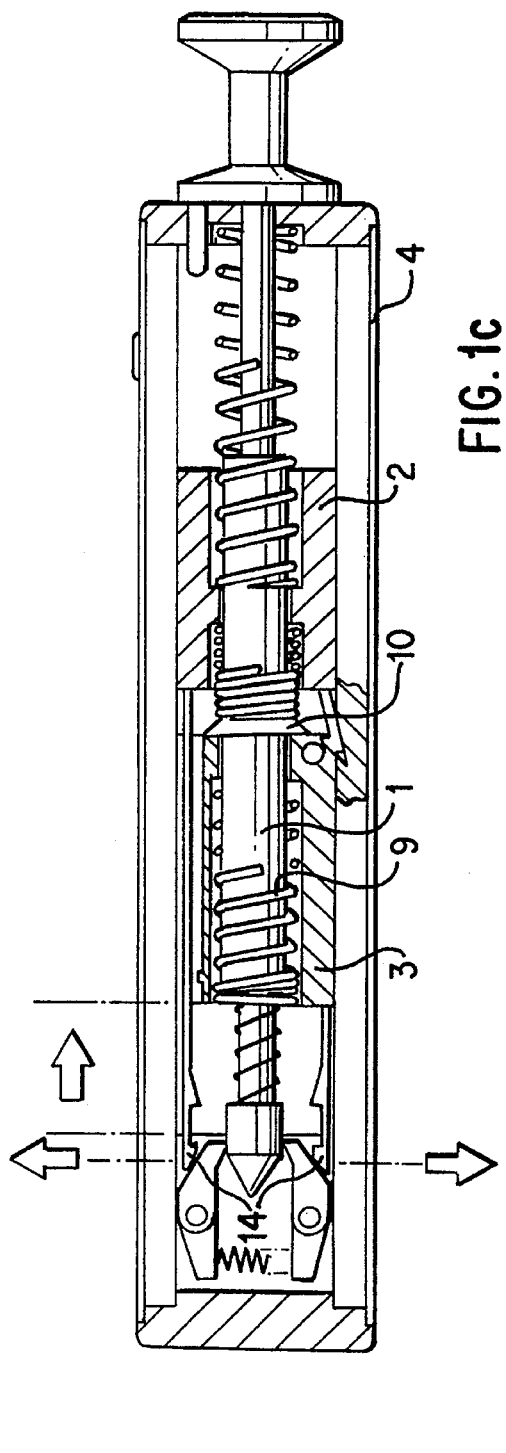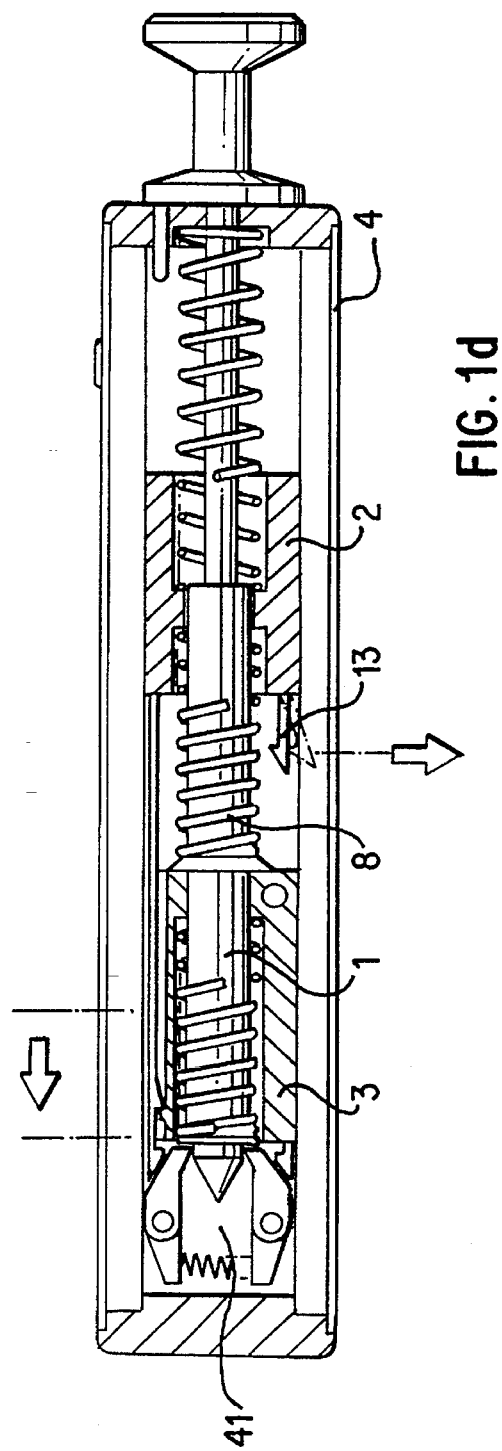

TISSUE SAMPLER

BACKGROUND AND SUMMARY OF THE INVENTION

This application is a continuation-in-part of U.S. application Ser. No. 08/143,389 filed on Oct. 29, 1993, abandoned, which is a continuation of U.S. application Ser. No. 07/995,934, filed on Dec. 22, 1992, which is abandoned, which is a continuation of U.S. application Ser. No. 07/671,908, filed as PCT/DE90/00549, Jul. 20, 1990 which is also abandoned.

The present invention relates to a tissue sampler, also referred to as a biopsy instrument.

In known devices of the generic type, a biopsy cannula provided with a cavity in its distal terminal zone is inserted into the tissue from which a tissue sample or specimen is to be taken. An exterior tube is then pushed over the biopsy cannula to sever a small tissue sample, located in the cavity, and the biopsy cannula is removed from the tissue together with the exterior tube pushed thereover.

One disadvantage of such prior art instruments is that the diameter of the biopsy cannula cannot be reduced below a certain size without impairing the stability required for the insertion of the needle into the tissue. Thus the exterior tube surrounding the biopsy cannula necessarily presents a comparatively great diameter, too.

An object of the present invention, therefore, is to provide a biopsy instrument (a device for taking tissue samples and specimens) wherein the diameter of the cannula, that is, the biopsy needle, and of the exterior tube pushed over the biopsy needle, may be substantially smaller than that of conventional prior art instruments, without risk of the needle element's bending when it is inserted into the tissue from which a sample is to be taken.

This and other objects and advantages are achieved according to the present invention, in which the inserting unit inserts the needle element into the tissue together with the exterior tube, the latter being in a position where it is pushed over the cavity. After the insertion is complete the exterior tube retracted to a position behind the cavity in the needle element. Due to this motion the tissue to be sampled advances into the cavity as a result of the "resilient resetting force" which is created by the cannula's displacement of the tissue. Then the exterior tube is again pushed over the cavity in the needle element (the biopsy needle), and the biopsy cannula is removed in this position.

Because the needle element is inserted into the tissue in combination with the exterior tube, it is not the needle element alone but rather the needle element in cooperation with the surrounding exterior tube which provides the necessary stability of the biopsy cannula in the instrument according to the invention. The needle element as such may therefore be made substantially thinner than the needle elements common in conventional biopsy instruments. On principle it is even sufficient to have an overall biopsy cannula of the same outside diameter as is commonly found in the biopsy needle itself in conventional instruments, and still achieve a cannula stability during insertion which is comparable to the stability of conventional instruments.

The inserting unit of the device according to the invention may be so designed that it carries out the individual successive movements automatically after operation of a "trigger element". It is preferable, however to design the inserting unit so that the operator can initially insert into a tissue only the needle element and the exterior tube surrounding the biopsy needle, whereupon the actual sampling (i.e. the process of taking tissue samples) is triggered manually. The operator thus has the option of correcting the location of tissue removal after insertion of the biopsy cannula should such a correction be required.

The inserting unit may include two coaxially displaceable slide elements, one of which (the slide element rearward in the direction of insertion) carries the needle element while the other (the one forward in the direction of insertion) carries a further slide element which is adapted to be displaced relative to the forward slide element and which supports the exterior tube. Because the three slide elements are displaceable jointly or relative to each other, it is possible for the inserting means to carry out the inventive succession of movements with selectable stroke lengths in a reproducible manner.

In principle, the individual slide elements may be driven in any known manner. A particularly simple structure is achieved, however, by providing springs to drive the individual slide elements. One embodiment of such a spring drive mechanism allows not only for a plain "biasing" of the inserting unit according to the invention, but also for an uncomplicated setting of the respective stroke lengths by means of stops.

Another advantageous embodiment of the invention provides biopsy cannulae whose designs are particularly expedient for the inventive succession of movements. With the specific configuration of the distal face of the exterior tube, the tissue sample is "severed" by a particularly smooth cut. Moreover, the contour of the exterior tube according to the present invention enhances the insertion of the exterior tube together with the biopsy needle.

Other objects, advantages and novel features of the present invention will become apparent from the following detailed description of the invention when considered in conjunction with the accompanying drawings.

BRIEF DESCRIPTION OF THE DRAWINGS

FIGS. 1a to 1d are schematic sectional views taken through an inserting unit according to the invention in various operating positions;

DETAILED DESCRIPTION OF THE DRAWINGS

Figure 1A:
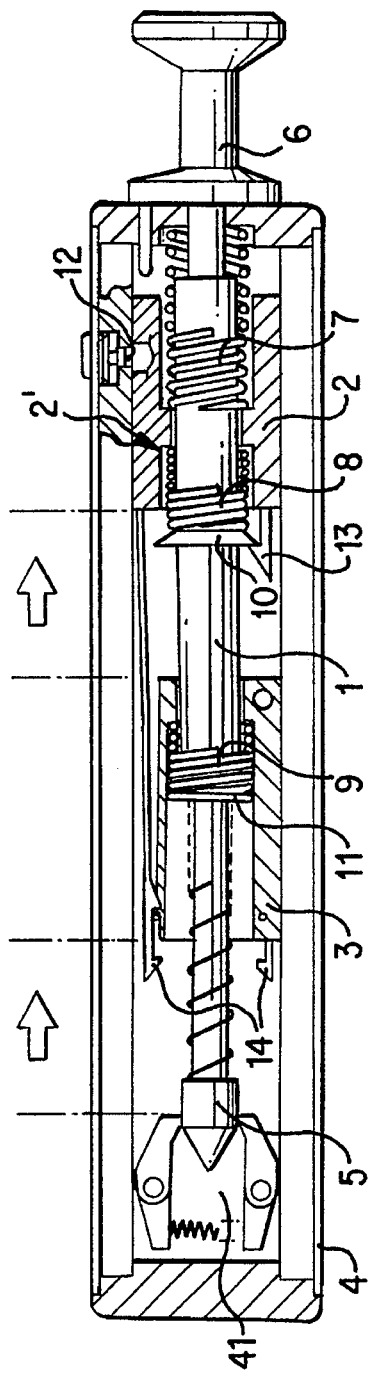

The inserting unit illustrated in FIGS. 1 and 2, which serves to insert biopsy cannulae, includes three slide elements (referred to simply as slides in the following) 1 to 3 supported in a housing 4 for displacement along a common axis 5. For simplicity, only one pin element 6 is shown as an example of the supporting elements on which the slide 1 is supported for displacement along the extension of the axis 5.

Compression springs 7 to 9 are provided to drive the various slides. Spring 7 is inserted between the casing 4 and the rear face of the slide 2, while spring 8 is located between a stop 10 at the slide 1 and a bearing surface 2' of slide 2, and spring 9 is clamped between another stop 11 at the slide 1 and the slide 3.

Pawls 12 to 14 are provided as trigger elements, pawl 12 being supported at the casing while the pawls 13 and 14 are provided at the slide 2. The pawls 12 and 14 engage into associated recesses in the slides 2 and 3, respectively, while the pawl 13 bears against the stop 10 of the slide 1.

Figure 2:
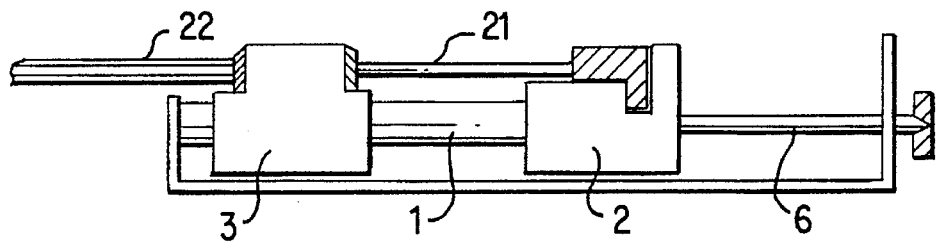
FIG. 2 illustrates the attachment of a biopsy cannula at an inserting unit in accordance with FIG. 1.

FIG. 2 illustrates the attachment of a biopsy needle 21 to slide 2, and the attachment of an exterior tube 22 of a biopsy cannula to slide 3. FIG. 2 shows a positive connection as an example of the interconnections between the elements 21 and 22 of the biopsy cannula, on the one hand, and the slide elements 2 and 3, on the other hand. Other connecting provisions are also conceivable, of course, the only requirement being that they allow for an uncomplicated attachment of the biopsy cannula at the inserting unit.

The following is a more detailed explanation of the operation of the inventive inserting unit with reference to FIGS. 1a to 1d as well as FIGS. 3a to 3d which illustrate each the respective positions of the biopsy cannula.

In the initial condition prior to initiation of the insertion procedure (in FIG. 1a), the compression springs 7 to 9 are compressed while the slide elements 1 to 3 are each arrested by the associated pawls or triggering elements 12 to 14. The cannula is retracted accordingly, with the exterior tube 22 covering the cavity 23 in the biopsy needle 21 FIG. 3a).

The sampling operation is started by actuation of the pawls or triggering elements 12. This action causes the slides 1 to 3 to be jointly displaced by the spring 7 along the axis 5. A stop 41 at the casing 4 limits the distance by which the three slides may be displaced; when expedient, the stop may be an adjustable arrester so that the advance motion for insertion of the biopsy cannula 21 and 22 may be selected.

Figure 1B:
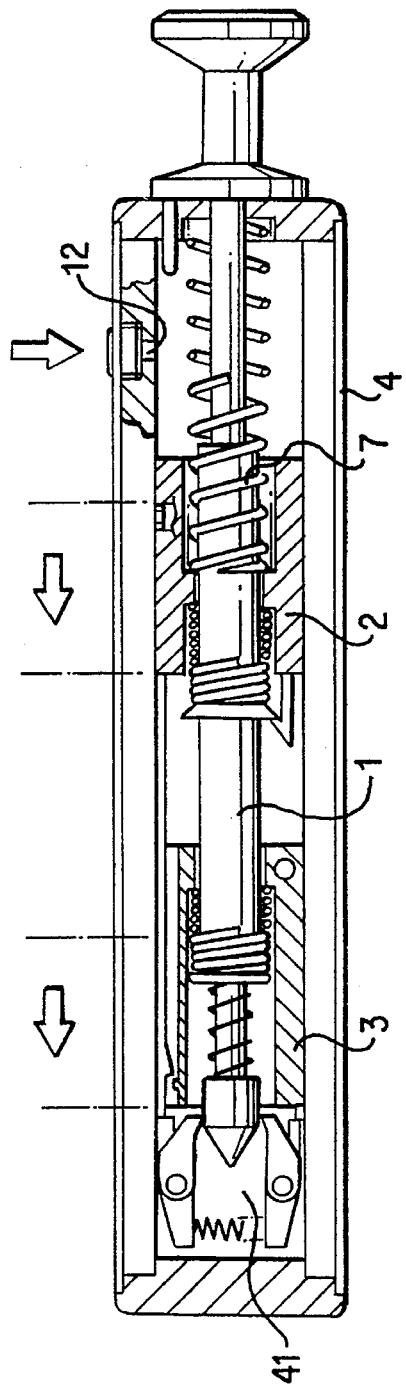
Figure 3A:
FIGS. 3a to 3d each show the various positions of the biopsy cannula associated with the positions of the inserting unit illustrated in FIGS. 1a to 1d.
Figure 3B:

FIG. 1b illustrates the condition of the inserting unit after insertion of the biopsy cannula. FIG. 3b shows the distal end of the biopsy cannula with this configuration. According to FIG. 3b, as a result of the joint movement of the individual cannula elements, the exterior tube 22 remains in a position pushed over the needle 21 so far that the cavity 23 in the needle 22 is covered.

With the elements in this position it is now possible to actuate the trigger element 14 either automatically under control of appropriate actuator elements such as a cam guide (not shown) at the casing 4, or manually. This operation initiates the movement of the slide 3 under the action of the spring 9 toward the stop 10.

Figure 3C:
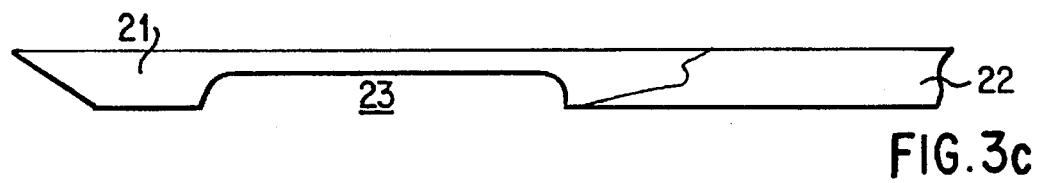

FIG. 1c shows the result of this movement for the inserting unit. FIG. 3c shows the retraction of the exterior tube 22 into a position behind the cavity 23 in the biopsy needle, which is caused by movement of the slide element 3 relative to the slides 1 and 2.

Figure 3D:
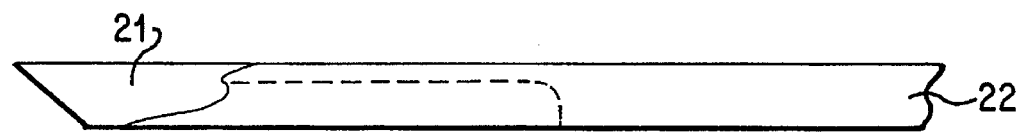

Then the triggered element 13 is actuated—also automatically (e.g. by means of an appropriate cam guide) or by hand—permitting the spring 8 to displace the slide 1 together with the slide 3 fixed to it in a direction toward stop 41 while the slide 2 remains stationary (FIG. 1d). As a result of this movement the exterior tube 22 is again pushed over the cavity 23 in the needle (FIG. 3d). The advancing movement of the exterior tube 22 separates that part of the tissue which has bulged into the cavity 23 due to its elasticity, from the remaining tissue, such that a small tissue sample is retained in the cavity 23, and may then be removed, e.g. by a suitable rearward movement of the inserting unit, with the biopsy cannula following as one unit consisting of the needle 21 and the exterior tube 22.

Figure 4A:
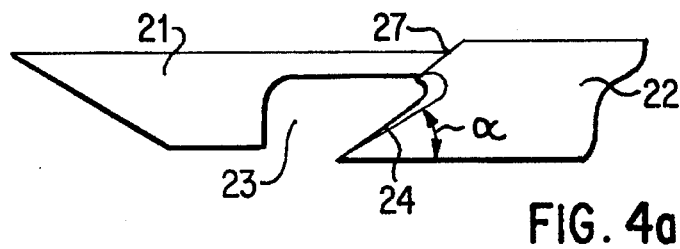
FIGS. 4a and 4b are enlarge views of the distal end of the biopsy cannula.
Figure 4B:
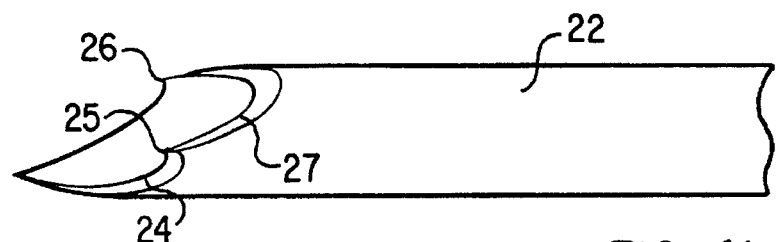

FIG. 4a shows an enlarged view of the needle 21 with cavity 23 and the exterior tube 22, and FIG. 4b is an enlarged view of the exterior tube 22 by itself. As may be seen in FIG. 4b, the distal end of the exterior tube 22 presents a first portion 24 which defines an acute angle α relative to the longitudinal axis of the exterior tube and is joined by a second portion 25 defining an obtuse angle relative to the longitudinal axis. The second portion 25 terminates in a pointed projection 26 which is located slightly above the center of the lateral contour in the illustrated embodiment. The pointed projection 26 is joined by a portion 27 which in turn defines an acute angle relative to the longitudinal axis. This specific shape of the distal end of the exterior tube is particularly expedient for the succession of motions provided according to the present invention, and ensures a safe and smooth severance of the tissue sample, even in cases where the specimen is removed in opposition to the extension of the fibers.

Figure 5A:
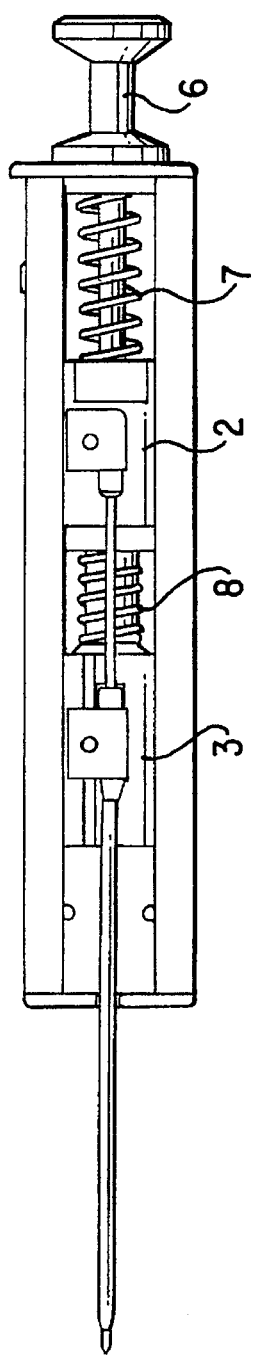
FIGS. 5a to 5c show the manner in which the elongated springs are retracted in an effortless way.
Figure 5B:
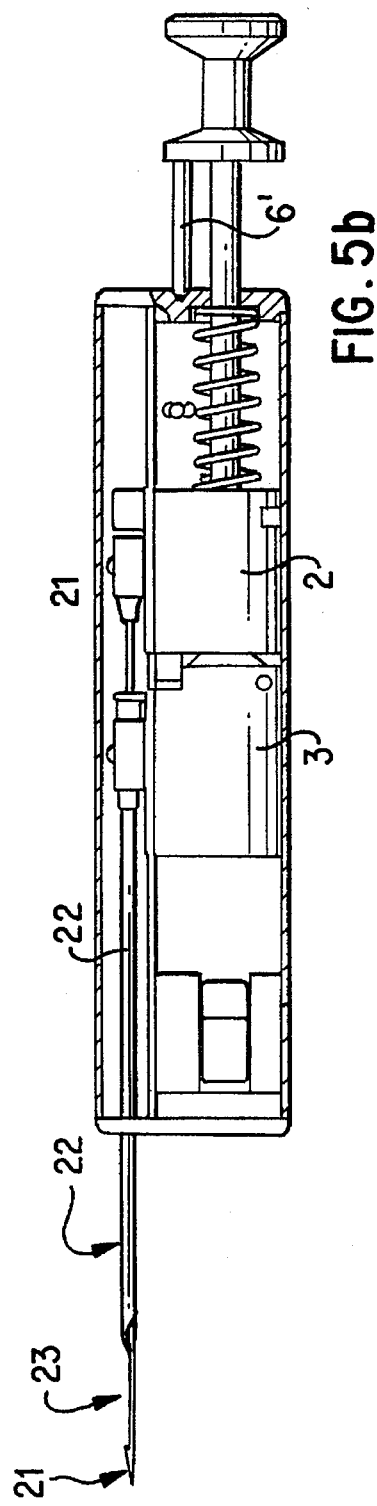
Figure 5C:
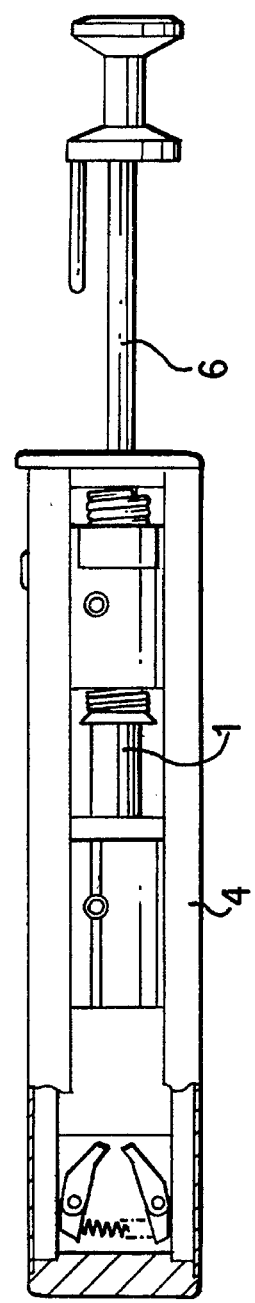

FIGS. 5a to 5c show the way to retract the elongated springs 7 to 9 in a very effortless manner. With the help of the described retracting system, a nurse is able to retract the biopsy pistol without the use of much power. Instead of a spring-arrangement with parallel arranged springs, the serial spring-arrangement can generally reduce the force required for retracting the elongated springs. For retracting the several springs, it is very convenient to retract every spring one after another, just to divide the way of retracting in different small pieces.

In FIG. 5, the final condition after the initiation of the inserting procedure is illustrated. All springs 7 to 9 are elongated (spring 9 is inside the housing of the slide 3 and is therefore not shown). For retracting the springs 7 to 9, the pin-element 6 has to be axially pulled out of the housing of the biopsy pistol. By pulling the pin-element 6 in a first step, the elongated spring 8 will be compressed until a distance pin 6' can be pushed against the outside wall of the biopsy pistol to compensate the force of th spring 8. In this configuration, the exterior tube 22 is positioned behind the cavity 23 of the biopsy needle 21. The sampling material of the examined body lays open in between the cavity 23 so that a nurse can extract the probe easily without applying any force to the biopsy pistol system.

By further pulling the pin-element 6 in the opposite direction of the biopsy pistol, the triggering element 13 (see FIG. 1d) interacts with the slide 3, so that the compressed spring 8 unfolds no more power.

By giving free the triggering elements 14 from the slide 3, the spring 9 can be compressed in a second step by pulling the pin-element 6 further until the slide 3 is moved forwardly into the direction of the stop 11 and is fixed in this position.

In FIG. 5c, the totally compressed configuration of the biopsy pistol is illustrated and can be reached in a third step by pulling the pin-element 6 a third time for compressing the spring 7 until the triggering element 12 interacts with the slide 2.

The above-mentioned mode of retracting the elongated springs is just only one possible way to retract. Other modes are possible regarding the succession of the retraction of the several springs.

Particularly, the choice of different spring-tensions leads to different ways of succession of the springs. The spring with the smallest tension is retracted first and so on.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. Device for removal of tissue samples by means of a biopsy cannula which comprises a needle element having a cavity in a distal terminal zone thereof and an exterior tube surrounding said needle element, and which is adapted to be inserted into tissue from which samples are to be taken by means of an inserting unit, wherein said inserting unit comprises first means for causing said needle element and said exterior tube to move together into a position inside the tissue, with said exterior tube covering said cavity, second means for retracting said exterior tube to a position behind said cavity in said needle element after termination of the inserting operation, whereby said cavity is opened to receive a tissue sample, and third means for subsequently pushing said exterior tube again over said needle element so as to cover said cavity.

2. Tissue sample according to claim 1, wherein the displacement of said exterior tube relative to said needle element may be triggered manually.

3. Tissue sampler according to claim 1, wherein said inserting unit comprises two coaxially displaceable slide elements, a first of said slide elements having said needle attached thereto and being located rearward, relative to the inserting direction, of the second of said slide elements, which carries a third slide element adapted to be displaced relative to said second slide element and which has said exterior tube attached thereto.

4. Tissue sampler according to claim 2, wherein said inserting unit comprises two coaxially displaceable slide elements, a first of said slide elements having said needle attached thereto and being located rearward, relative to the inserting direction, of the second of said slide elements, which carries a third slide element adapted to be displaced relative to said second slide element and which has said exterior tube attached thereto.

5. Tissue sampler according to claim 3, wherein a first spring acts upon the first and second two coaxially displaceable slide elements in the inserting direction, and wherein said two slide elements are adapted to be arrested by a releasable locking element in the position in which the spring is biased.

6. Tissue sampler according to claim 4, wherein a first spring acts upon the first and second two coaxially displaceable slide elements in the inserting direction, and wherein said two slide elements are adapted to be arrested by a releasable locking element in the position in which the spring is biased.

7. Tissue sampler according to claim 5, wherein said second slide element comprises a stop for said third slide element, with said third slide element being adapted to be moved toward said stop under the action of a second spring, following the release of a locking element.

8. Tissue sampler according to claim 7, wherein a third spring is provided and biased between said two coaxially displaceable slide element, said third spring being adapted to cause said second and third slide elements to advance together in a cannula-inserting direction after release of a locking element, whereby said third slide element is advanced to a position where it was located with said second spring in a compressed state.

9. Tissue sampler according to claim 3, wherein adjustable stops are provided to limit the displacement of said slide elements.

10. Tissue sampler according to claim 8, wherein a retracting system of the elongated springs-after an insertion procedure is provided to compress the three springs one after another.

11. Tissue sampler according to claim 10, wherein a distance pin is provided for extracting a sampling probe out of the cavity of the needle element without applying any force onto the pin-element.

12. Tissue sampler according to claim 10, wherein every spring provides a triggering element for securing the spring in the compressed form.

13. Cannula for use with a device for removal of tissue samples comprising a needle element having a cavity in a distal terminal zone thereof and an exterior tube surrounding said needle element, and which is adapted to be inserted into tissue from which samples are to be taken by means of an inserting unit wherein said inserting unit comprises first means for causing said needle element and said exterior tube to move together into a position inside the tissue with said exterior tube covering said cavity, second means for retracting said exterior tube to a position behind said cavity in said needle element after termination of the inserting operation, whereby said cavity is opened to receive a tissue sample, and third means for subsequently pushing said exterior tube again over said needle element so as to cover said cavity, wherein a distal end of said exterior tube includes a first portion defining an acute angle relative to a longitudinal axis of said exterior tube, which is joined by a second portion, defining an obtuse angle relative to said longitudinal axis of said exterior tube.

14. Cannula according to claim 13, wherein said second portion terminates in at least one pointed projection.

15. Cannula according to claim 14, wherein said pointed projection is located in the center of a lateral contour or above a center of a lateral contour of said exterior tube.

* * * * *